(12) United States Patent
Bert et al.

(10) Patent No.: US 9,586,058 B2
(45) Date of Patent: Mar. 7, 2017

(54) IRRADIATION OF A TARGET VOLUME, TAKING INTO ACCOUNT A VOLUME TO BE PROTECTED

(75) Inventors: Christoph Bert, Aschaffenburg (DE); Eike Rietzel, Weiterstadt (DE); Gerhard Kraft, Darmstadt (DE)

(73) Assignee: GSI Helmfoltzzentrum fur Schwerinonenforschung GmbH, Darnstadt (DE)

( * ) Notice: Subject to any disclaimer, the term of this patent is extended or adjusted under 35 U.S.C. 154(b) by 470 days.

(21) Appl. No.: 13/125,888

(22) PCT Filed: Oct. 17, 2009

(86) PCT No.: PCT/EP2009/007462
§ 371 (c)(1),
(2), (4) Date: Jun. 16, 2011

(87) PCT Pub. No.: WO2010/049072
PCT Pub. Date: May 6, 2010

(65) Prior Publication Data
US 2011/0306818 A1    Dec. 15, 2011

(30) Foreign Application Priority Data
Oct. 27, 2008    (DE) .................. 10 2008 053 611

(51) Int. Cl.
*A61N 5/10*    (2006.01)

(52) U.S. Cl.
CPC ........... *A61N 5/103* (2013.01); *A61N 5/1043* (2013.01); *A61N 2005/1087* (2013.01)

(58) Field of Classification Search
CPC .... A61N 5/103; A61N 5/1031; A61N 5/1038; A61N 2005/1034; A61N 2005/1087; A61N 5/1043

USPC ............................................... 600/1; 378/65
See application file for complete search history.

(56) References Cited

U.S. PATENT DOCUMENTS 5,602,892 A    2/1997  Llacer
5,647,663 A    7/1997  Holmes
(Continued)

FOREIGN PATENT DOCUMENTS

EP    1238684 A1    9/2002
EP    1818078 A1    8/2007
(Continued)

OTHER PUBLICATIONS

Muren, Ludvig P.et al"Testing the New ICRU 62 'Planning Organ at Risk Volume' Concept for the Rectum" RadiotherapyandOcology, Elsevier Bd75,Nr3,Jun. 1, 2005 Seiten293-302.
(Continued)

*Primary Examiner* — Charles A Marmor, II
*Assistant Examiner* — Thaddeus Cox
(74) *Attorney, Agent, or Firm* — Reising Ethington P.C.

(57) ABSTRACT

The idea concerns irradiation of a target volume (53), wherein intensities for target points (70) are determined which are sequentially approached by a beam, comprising the following steps: detecting a volume (63) to be protected, wherein a dose generated by irradiating a target volume (53) does not exceed a predetermined maximum value; determining intensities for target points (70) in such a way that within the volume (63) to be protected the generated dose does not exceed the predetermined maximum value, wherein a dose contribution data record is used for determining the intensities, which dose contribution data record comprises the dose generated at other spots (73) by directing the beam (10) on one of the target points (70) with a predetermined intensity.

20 Claims, 4 Drawing Sheets

(56) References Cited

U.S. PATENT DOCUMENTS

Figure 1:
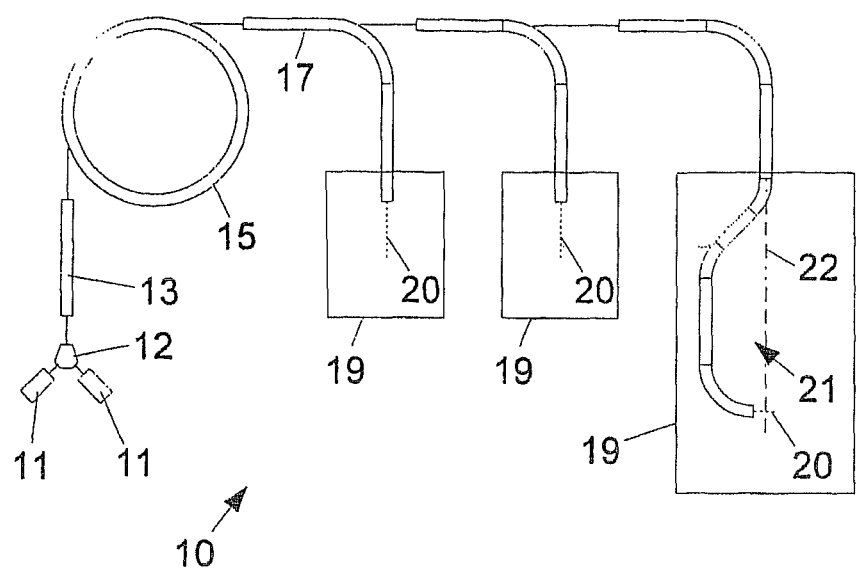

| | | | |
|---|---|---|---|
| 6,260,005 | B1 | 7/2001 | Yang et al. |
| 7,102,144 | B2 | 9/2006 | Matsuda et al. |
| 2003/0212325 | A1* | 11/2003 | Cotrutz et al. ............... 600/436 |
| 2005/0201516 | A1* | 9/2005 | Ruchala et al. ............... 378/65 |
| 2006/0067469 | A1* | 3/2006 | Dooley et al. ............... 378/65 |
| 2007/0041497 | A1 | 2/2007 | Schnarr et al. |
| 2007/0053490 | A1* | 3/2007 | Wang et al. ............... 378/65 |
| 2007/0127623 | A1 | 6/2007 | Goldman et al. |
| 2007/0228305 | A1 | 10/2007 | Keppel et al. |
| 2008/0219407 | A1* | 9/2008 | Kaiser et al. ............... 378/65 |
| 2008/0317204 | A1* | 12/2008 | Sumanaweera et al. ....... 378/65 |
| 2011/0306818 | A1 | 12/2011 | Bert et al. |

FOREIGN PATENT DOCUMENTS

| | | |
|---|---|---|
| JP | 2006087649 | 4/2006 |
| WO | WO 03076003 A2 | 9/2003 |
| WO | WO 2007079854 A2 * | 7/2007 |
| WO | WO 2008116596 | 10/2008 |
| WO | WO 2008116596 A1 * | 10/2008 |

OTHER PUBLICATIONS

McKenzie, Alan et al "Margins for Geometric Uncertainty Around Organs at Risk in Radiotherapy" Radiotherapy and Oncology, Elsevier Bd 62 Nr3, Mar. 1, 2002 Seiten299-307.

(German Office Action) Deutsches Patent—Und Markenamt 80297 Munchen Date: May 11, 2009.

Universitats Klinikum Heidelberg Website Facts and Figures 2pgs Date: Jul. 12, 2013.

Universitats Klinikum Heidelberg Website Accelerator Facility 2pgs Date: Jul. 12, 2013.

Edward L. Ginzton, et al. "Clinical Usefulness of High Energy Beams History of Microwave Electron Linear Accelerators for Radiotherapy" Int. J. Radiation Oncology Biol Phys. vol. 11, pp. 205-216 Date: Sep. 5, 1984.

Varian Clinac 18R, 1800, 2100C, 2300C/D Equipment Information Dated: Feb. 1992 pp. 18.

E. Vigneault, et al. "MOBETRON: Ein mobiler Elektronenbeschleuniger im Operationssaal" Centre Hospitalier Universitaire de Quebec, Pavillon L'Hotel-Dieu de Quebec, Radiotherapy Dept. 11, Cote du Palais, Quebec, G1R 2J6, Kanada.

Eugene Wong, Ph. D., Jeff Z. Chen Ph. D. and Jonathan Greenland, M.D., Title: Intensity-Modulated Arc Therapy Simplified, International Journal of Radiation: Oncology Biology Physics, Pergamon Press, USA, vol. 53, No. 1, pp. 222-235, 2002; XP007907774.

Cedric X. Yu et al., Title: Clinical Implementation of Intensity-Modulated Arc Therapy, International Journal of Radiation; Oncology Biology Physics, Pergamon Press, USA, vol. 53, No. 2. pp. 453-463, 2002; XP007907772.

European Office Action, Serial No. 09744 065.5-1652, Ref. No. 11GSI0101EPP, Date: Jun. 5, 2015, Applicant: GSI Helmholtzzentrum fur Schwerionenforschung GmbH, et al.

* cited by examiner

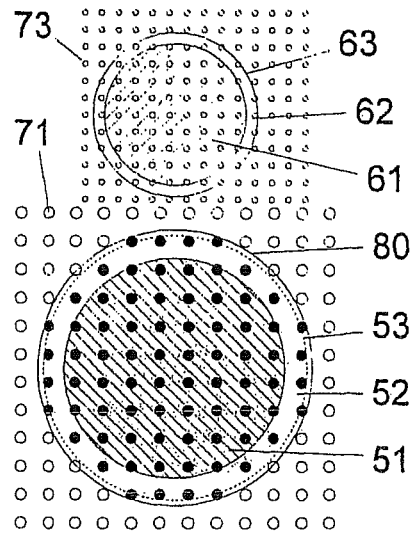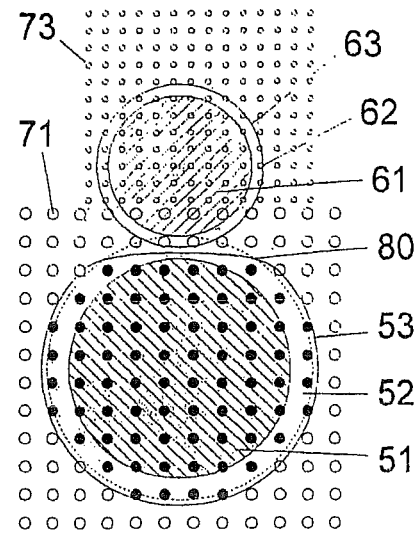
Fig. 3　　　　　　　　Fig. 4
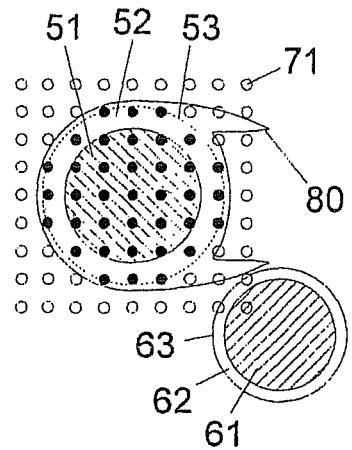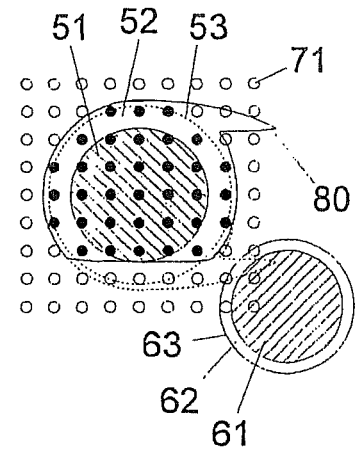
Fig. 5　　　　　　　　Fig. 6

Dividing in several session

Detecting

Scanning

Tracking

Considering a pre-dose

Preparing a dose contribution data record prior to irradiation

Correcting the dose contribution data record after detection

Newly preparing a dose contribution data record after detection

Changing of target volumes or volumes

Fig. 8

IRRADIATION OF A TARGET VOLUME, TAKING INTO ACCOUNT A VOLUME TO BE PROTECTED

The invention concerns a method for planning irradiation with a beam approaching target points, an appropriate method for irradiation, a device for a corresponding irradiation, and a control system for controlling such a device.

The irradiation of a target with a beam approaching different target points (beam scanning) is already known. For example, when irradiating tumors, particle beams, especially ion beams, which have in particular protons, α particles or carbon nuclei, are used. The beam sequentially approaches parts of the target region, the target points.

A target point is a spot which can be defined, for example, by indicating three Cartesian space coordinates (x, y, z) and which is usually located within the object to be irradiated, especially within the target volume or its surrounding area.

When scanning with a particle beam, the particle beam is usually deflected by deflecting magnets in two mutually perpendicular directions (x and y direction). By actively varying the particle energy, the position of the Bragg-Peak, wherein the largest proportion of the dose is deposited, is adjusted to different depths (z direction) in the target. Frequently, spatial target reagions are irradiated in layers wherein the energy determining the depth of penetration is selected to be constant in each layer (iso-energy layer). Also known is the so-called depth scanning wherein the sequentially approached target points are not necessarily assigned to individual (iso-energy) layers. Basically, the invention concerns even embodiments wherein the beam is formed by electromagnetic waves.

Scanning methods allow for irradiation that is adapted to the shape of the target by scanning with a beam. There are different types of scanning methods. Grid scanning proved to be an especially effective method. For this method, a three-dimensional grid is placed on the volume to be irradiated. Here the particle beam lingers at each of several screen dots is during a predetermined time period or deposits at each screen dot a predetermined number of particles. However, between the screen dots, the particle beam is not or not always turned off. However, in principle, the invention is not restricted to grid scanning but can be used also in connection with spot scanning, a continuous or discontinuous scanning method, or with other scanning methods.

When using grid scanning, it should be noted that the screen dots can differ from the target points. For example, target points usually apply only to a portion of the screen dots because generally not all screen dots are approached. Furthermore, the screen dots and the target points can usually be indicated in different coordination system, for example, in a fixed coordination system and a coordination system which is based on the target volume to be irradiated. Therefore, the target points do not have to be mutually congruent. It is also possible to indicate screen dots and target points in a mutual coordination system.

Here, a target volume denotes a spatial region within which a dose is to be deposited that has been predetermined or prescribed by an operator, for example, medical staff.

A particle beam is a beam with a defined cross-section consisting of particles with a defined, usually small spectrum of the particle energy. The particle energy comprises the energy that the individual particle has when entering the object to be irradiated.

When referring to a particle beam which is directed to a target point it is indicated that the particle beam is deflected in x and y direction (for example, by deflection magnets) in such a way that the target point is located, for example, in the center or on a line (or its extension) of maximum fluence or dose, and that the target point is located in the Bragg-Peak of the particle beam. We also talk about approaching a target point.

In planning an irradiation, particularly the following parameters are determined per target point or per screen dot: lateral position (x and y direction), energy—determining the depth of penetration, focus and number of particles.

Usually, for example, in irradiating a tumor, it is the objective to permeate the target volume with a specific distribution of the dose, i.e., to achieve a target dose distribution, in particular a biologically effective target dose distribution. For example, the target dose distribution is quantified as deposited energy per volume unit. A commonly used method is to indicate the dose in joules per kilogram (Gray).

For example, after thorough examination, the user determines or prescribes the dose, which is to be applied as function of location. For example, the dose should show a predetermined value distribution within a target volume, especially a tumor. Outside of the tumor the dose should drop as quickly as possible, and especially in organs to be protected or organs at risk (OAR) the dose should not exceed a predetermined maximum value, for example, quantified as maximum dose, DVH condition, EUD, also called tolerance dose. Examples for organs at risk are the rectum during irradiations of the prostate gland and certain structures inside the lung during lung tumor irradiations.

The invention is based on the objective of providing an advantageous method for planning irradiation by taking into consideration a volume to be protected, an appropriately advantageous method for irradiation, a correspondingly advantageous device for irradiation and an advantageous control system for controlling such a device.

The objective is achieved by a method for planning the irradiation of a target volume, wherein intensities for target points are determined that are to be approached sequentially by a beam, comprising the following steps: detecting a volume to be protected, wherein a dose generated by irradiating the target volume should not exceed a predetermined maximum value; determining intensities for target points in such a way that within the volume to be protected the generated dose does not exceed the predetermined maximum value of scheduled irradiation. At the same time, a dose contribution data record is used for determining the intensities which dose contribution data record comprises the dose that is generated for target points at other spots in scheduled irradiation by directing the beam with a predetermined intensity on one of the target points.

Preferred embodiments of the invention are shown in the dependent claims and are subsequently described in more detail.

A method "for planning irradiation" does not have to include irradiation but can be performed independent of irradiation. In particular, the process of planning can precede the process of irradiation. To simplify matters the description does not always differentiate the two processes. The previous and following description of the individual process characteristics applies to the process of planning, as well as to the process of irradiation, without specifically mentioning it in each particular case.

The invention is based on the assessment that at times it is more important to protect the volume to be protected, especially an OAR, than to cover the target volume with the scheduled dose. For example, this can be the case when an extremely high dose has been prescribed for the target volume but a lower dose would be sufficient for the target volume, especially for tumor control. Accordingly, it is possible in such cases to accept a slight underdosage of the target volume if it is absolutely necessary to protect one or several volumes to be protected, especially if they involve organs at risk.

Furthermore, the invention is based on the experience that irradiation typically takes place in several sessions, especially in fractions in case of fractioned irradiation wherein only a small fraction of the entire dose to be applied is deposited in each session. Basically, irradiation in several sessions is advantageous, especially because it is possible to average errors by means of statistical effects and to increase the normal tissue dose tolerance.

For example, usually the intervals between fractions amount to one or several days. Fractioned irradiation usually covers several weeks. Within this time period it is possible for the target volume, as well as for the volume to be protected, for example, an organ at risk, to change its position, size and/or shape.

To be able despite changes not to fall below a predetermined minimum dose within the target volume and not to exceed a predetermined maximum volume within the volume to be protected, the target volume usually has a safety margin. When the safety margin has been applied to the target volume, the desired dose is assigned to the target volume. It is also possible to apply a safety margin to the volume to be protected. However, frequently it is necessary to apply extensive safety margins in order to take into consideration possible changes within the long period of time required for covering all sessions.

This can result in situations that significantly aggravate irradiation planning. In particular, it is possible that the safety margins involving the target volume overlap with the volumes to be protected when the internal anatomy changes, or when changes in position of the target volume result in dose increases in the volume to be protected. Moreover, it is also possible that the range of irradiation changes as a result of anatomic changes which can result in additional depositions in the volume to be protected.

Depending on the structure to be irradiated, respective relative motions can be relevant even in shorter time scales. For example, when irradiating a person, the time scale shows motions of fractions of a second (heartbeat), of seconds (breathing), and minutes, hours or days (changes in anatomical structure, for example, intestinal movements).

Also the intervals between sessions can vary quite a bit. For example, it is possible to have one session per day or several sessions per day. In special multiple irradiations, for example, the sessions can comprise merely a few seconds or a few minutes.

The invention can be used advantageously even with such short time scales.

The present invention is also based on the idea of detecting a volume to be protected, wherein a dose generated by irradiating the target volume should not exceed a predetermined maximum value, prior to irradiation or a session of irradiation, especially prior to applying a fraction. In particular, the volume to be protected comprises one or several organs to be protected or organs at risk and optionally safety margins surrounding these organs. For different target points, preferably for each target point within the target volume, the intensity of irradiation, especially the number of particles is determined in such a way that within the volume to be protected the generated dose does not exceed the predetermined maximum value. For this purpose, a dose contribution data record is used which comprises for different target points, preferably each target point, the dose which has been generated at other spots in the object or body by directing the beam with a predetermined number of particles on the target point or one of the target points.

The maximum value is also described as threshold value. In a simple case, this threshold value can actually correspond to a scalar dose value, but also to an especially spatial distribution. However, the threshold value can also be selected with a view to the biological effect by considering, for example, the equivalent uniform dose or as a biologically effective dose. It is also possible to use other parameters corresponding to a dose or dose distribution.

The volume to be protected and/or the target volume can be detected especially by means of X-ray tomography, ultrasonic diagnostic or sonography, optical coherence tomography, magnetic resonance imaging or nuclear magnetic resonance, computer tomography, positron emission tomography, single photon emission computed tomography (SPECT), electromagnetic impedance tomography (EMIT), neutron tomography or other methods which can be used for three-dimensional or even 2D or 4D imaging of the body or parts of the body to be irradiated. During the process of recording it is possible to detect especially changes in position, size and/or shape, even independent of each other, at least of the volume to be protected or the target volume in comparison to the situation on which the original radiation plan was based, or in comparison to the situation of previous sessions.

The dose contribution data record can be prepared prior to the first session or prior to the first fraction and can optionally be corrected on the basis of imaging methods after the volume to be protected has been detected. Alternatively, the dose contribution data record is newly prepared after the volume to be protected has been detected.

When determining the intensities, especially the number of particles, it is possible besides the dose contribution data record to take into consideration the pre-dose generated in the object or body in one or several of the preceding sessions.

Preferably, the target points are approached in the context of grid scanning. It is possible to assign a separate grid to each individual target volume. However, it is also possible to imbed all target volumes in one grid.

Usually several screen dots are located within one target volume to which the target dose distribution has been assigned. In this respect, it is possible to speak of a target dose per screen dot, or a screen dot target dose. In this way of speaking, according to the invention, the screen dot target doses are determined in such a way that a predetermined maximum value is not exceeded within the volume to be protected.

The target volumes or the respective screen dots can be tracked to the structures to be irradiated. We also speak of an adaptation, wherein the term adaptation in this context refers especially to the position of the points to be irradiated. Subsequently, this tracking method is described in more detail and it is also described in detail in DE 10 2006 044 139. In the case of such tracking, which here involves, for example, irradiation of a tumor using grid scanning, the x and y positions of the screen dots, as well as the energy required for the actual anatomy are determined. According the DE publication mentioned above, the volumes are first registered to each other and the specific transformation parameters are applied to the screen dot positions in the anatomy, and the required energy has to be newly determined by means of the actual anatomy. It is possible, in turn, that an interpolation for a regular grid is required, and that the number of particles per screen dot has to be adjusted. In this case, it has to be taken into account that the prepared dose contributions do not undergo transformation but are newly set up or are determined from the ones that were prepared. Transformations can be performed for the anatomy as a whole or for the individual target volumes.

When the target volume comprises a safety margin, collectively also called planning target volume, the intensities can be determined in such a way that the deposited dose exceeds a predetermined minimum value within the planning target volume, preferably in the internal region surrounded by the safety margin. At the same time, the intensities preferably can be determined in such a way that the deposited dose does not exceed a predetermined maximum value within the volume to be protected. Furthermore, when the volume to be protected comprises an organ to be protected and a safety margin surrounding the organ to be protected, the intensities can be determined in such a way that the deposited dose within the organ to be protected does not exceed the predetermined maximum value. In simple cases, the intensities can be determined in such a way that the beam is not directed to target points located within an overlapping region of the target volume and the volume or organ to be protected, especially not on an overlapping region of the safety margin of the target volume and the safety margin surrounding the volume to be protected.

If there would be no changes in the object to be irradiated, the data records for all sessions could be selected similarly. Changes taking place between the sessions result in differences between the data records of the individual sessions. The described determination of the intensities can be depicted as an adaptation of intensities to the changes in the object to be irradiated. During a repetition of the described method prior to selected or all sessions, it is possible to detect systematic changes which indicate that it would be advantageous to supply a completely new preparation or new optimization of the radiation plan instead of a repeated adaptation of the radiation plan or the data record.

Preferably, the dose applied in a particular session is calculated after each session. In this way, it is possible to monitor the course of the irradiation.

In particular, it is preferred to determine, especially calculate, the amount of all previously applied doses after each session.

By means of such a subsequent determination, it is possible to consider and possibly adjust a pre-dose in case of a new irradiation optimization by applying, for example, the difference to the prescribed dose in consideration of possible fractioning effects.

In case of deviations, it is thus possible to perform, a new optimization of the irradiation plan by taking into consideration the already applied dose. In this way, it is especially possible to detect existing systematic deviations which indicate that a completely new irradiation plan should be prepared and optimized instead of adapting or correcting an available radiation plan from session to session.

When the position and/or shape of at least one of the target volumes and/or the volume to be protected changes, it is possible to exceed the predetermined maximum value for the dose within the volume to be protected, especially when the position of at least one target volume changes in relation to the volume to be protected.

In the event that an irradiation plan already exists, it is preferred to change this plan because of the change in position and/or shape instead of preparing a new irradiation plan.

A changed dose is applied particularly to those target points which otherwise would result in an excessive dose. Possibly, this involves only a small portion of all target points. This involves especially the target points of a safety margin. In a simple case, target points are no longer or newly approached.

This can be especially implemented in that different spatial positions and/or shapes of at least one of the target volumes and/or the volume to be protected are taken into consideration in advance. In this way, it is especially possible to pre-calculate for target points that are located in one of the safety margins different dose contributions, depending on the different spatial positions and/or shapes of at least one of the target volumes or the volumes to be protected. This is advantageous since especially with these target points an incorrect dose often results from changes in position or shape of at least one of the target volumes and/or the volume to be protected. Then, when a change in position or shape actually occurs, the pre-calculated dose contributions can be used for changing an already existing irradiation plan. In this way, it is possible to quickly respond to the change in position or shape and adapt the irradiation plan.

Advantageously, the intensities determined according to the invention, especially numbers of particles, form a data record which is preferably suitable for controlling an irradiation system used to irradiate the target volume with a beam in a continuous or discontinuous process.

The dose contribution data record for the individual target points in different depths can be generically available so that they do not have to be calculated each time and, in addition, dose contributions can be entered with the generic approach.

Preferably, the generated data record can be used as control data, which is used to control a device for irradiating, especially during the application of a session. Moreover, the data record can define the coordinates or x and y positions and the particle energies or the respective z positions of the target points. Even these coordinates can be adjusted respectively on the basis of imaging methods, in particular tomographic data.

It should be emphasized again that the dose contribution data record can comprise in particular even dose contributions outside of the target volume.

Besides irradiation of humans or animals, irradiation of organic material, especially cells, or irradiation of inorganic material, for example, plastic material, is relevant; for example, in the context of materials research.

The objective is also achieved by a method for irradiating a target volume, wherein intensities for target points are determined which are sequentially approached with a beam, comprising the following steps: detecting a volume to be protected, wherein a dose generated by irradiating the target volume should not exceed a predetermined maximum value; determining intensities for target points in such a way that within the volume to be protected the generated dose does not exceed the predetermined maximum value, wherein a dose contribution data record is used for determining the intensities, which dose contribution data record comprises for target points the dose generated at other spots by directing the beam to one of the target points with a predetermined intensity.

Preferably, the method for irradiation comprises the previously described method of planning an irradiation; in particular also in one of the preferred embodiments of the planning method. In particular, the irradiation method can comprise the generation of a data record for controlling the device. For example, the data record can be entered on a data carrier and then be read to control the device. In a special embodiment, the steps of generating and controlling are repeated for each session, especially for each fraction of a fractioned irradiation.

The objective is further achieved by a device for irradiating a target volume with a radiation source and a control system for controlling the device, wherein the device is designed to determine by means of the control system intensities for target points which are sequentially approached by the beam. The device is designed to detect a volume to be protected wherein a dose generated by irradiating the target volume should not exceed a predetermined maximum value. The intensities for target points are determined in such a way, that within the volume to be protected the generated dose does not exceed a predetermined maximum value, wherein a dose contribution data record is used for determining the intensities which dose contribution data record comprises for target points the dose generated at other spots by directing the beam to one of the target points with a predetermined intensity.

Such an irradiation device comprises a radiation source, especially for generating a particle beam, in particular an ion beam. The radiation source can consist of an accelerator, especially a synchrotron or cyclotron.

When irradiation takes place by means of an ion beam, the irradiation device comprises also a scanning device, or scanner, comprising scanning magnets for deflecting the ion beam.

Preferably, the device for irradiation is designed to perform one of the methods described above, especially in one of the preferred embodiments for performing the methods.

The objective is also achieved by a control system for controlling a device for irradiating a target volume, wherein by means of the control system the device is designed to determine intensities for target points which can be sequentially approached with a beam, to detect a volume to be protected wherein a dose generated by irradiating a target volume should not exceed a predetermined maximum value; to determine intensities for target points in such a way that within the volume to be protected the generated dose does not exceed the predetermined maximum value, wherein a dose contribution data record is used for determining the intensities, which dose contribution data record comprises for target points the dose generated at other spots by directing the beam to one of the target points with a predetermined intensity.

In contrast to the irradiation device, the control system is does not comprise a radiation source. When the control system is used for controlling an irradiation device for irradiating humans or animals, it is also called a treatment control system (TCS). Preferably, the control system comprises at least one device for detecting the parameters of the irradiation device, for example, the scanner settings and beam properties, and/or it comprises a device for detecting the structures to be irradiated. In this way, the control system can have an input for receiving an image of an imaging system, for example, a tomograph.

The control system can be implemented with the help of a computer or a computer system. For example, such a computer can store information regarding the energy distribution of the sessions and the iso-energy layers, the target points, the screen dots, the target dose per screen dot, the treatment plan or criteria for terminating irradiation. For example, one criterion for terminating irradiation can be that the target dose per target point specified in the treatment plan has been reached. It is useful to store the target dose per target point in a table.

Preferably, the control system is designed for controlling one of the devices for irradiation described above; in particular in one of the preferred embodiments of the irradiation device. In particular, the control system is designed to control a method according to the invention on a device according to the invention.

Basically, the invention concerns also a respectively advantageous method for generating a data record, in particular based on the planning method, a method for controlling an irradiation device, in particular based on the irradiation method, and a respectively advantageous computer program product based on the invention.

Basically, the invention concerns also a method and a device for determining control parameters of an irradiation system for irradiating a predetermined target volume with a scanning method.

The previous and the following description of the individual characteristics refers to all objects according to the process category, as well as the device category without specifically mentioning it in each particular case. The individual characteristics disclosed in this way can also form a substantial part of the invention in combinations not shown in this context.

The previous and the following description of the individual characteristics refers also to the computer program product with program code for performing or controlling invention-based methods and/or for the implementation on a computer/processor.

Furthermore, the invention can be implemented as a computer program product by means of a program code stored on a machine-readable carrier, for example, a ROM, EPROM, EEPROM, or flash memory, a CD ROM or DVD, or on a disc or hard drive, or in the form of firmware, for performing one of the methods mentioned when the computer program product runs on a computer or processor.

It is also possible to implement the present invention as digital storage medium, for example, ROM, EPROM, EEPROM, or flash memory, CD ROM or DVD or disc or hard drive, with electronically readable control signals, which can interact with a programmable computer or processor system in such a way that one of the methods discussed can be performed.

Figure 2:
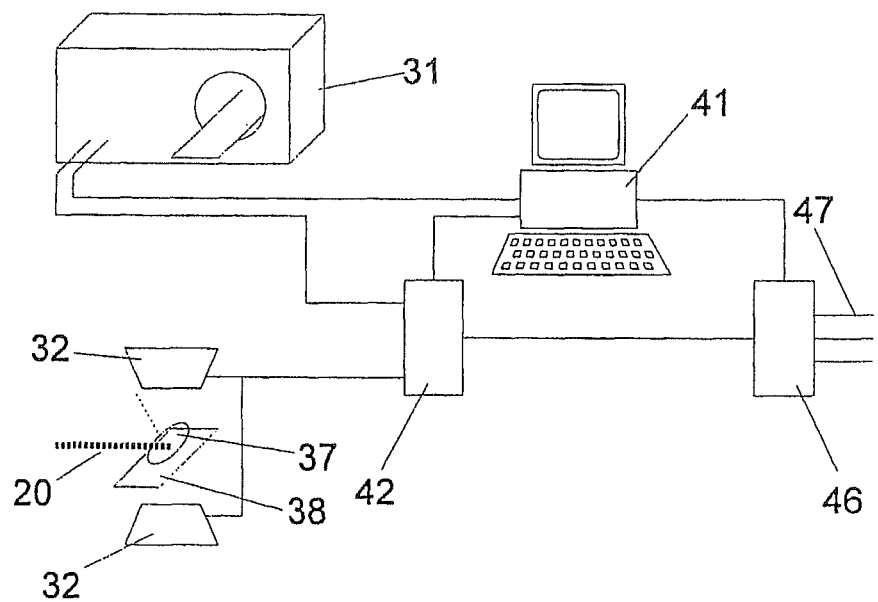
Figure 7:
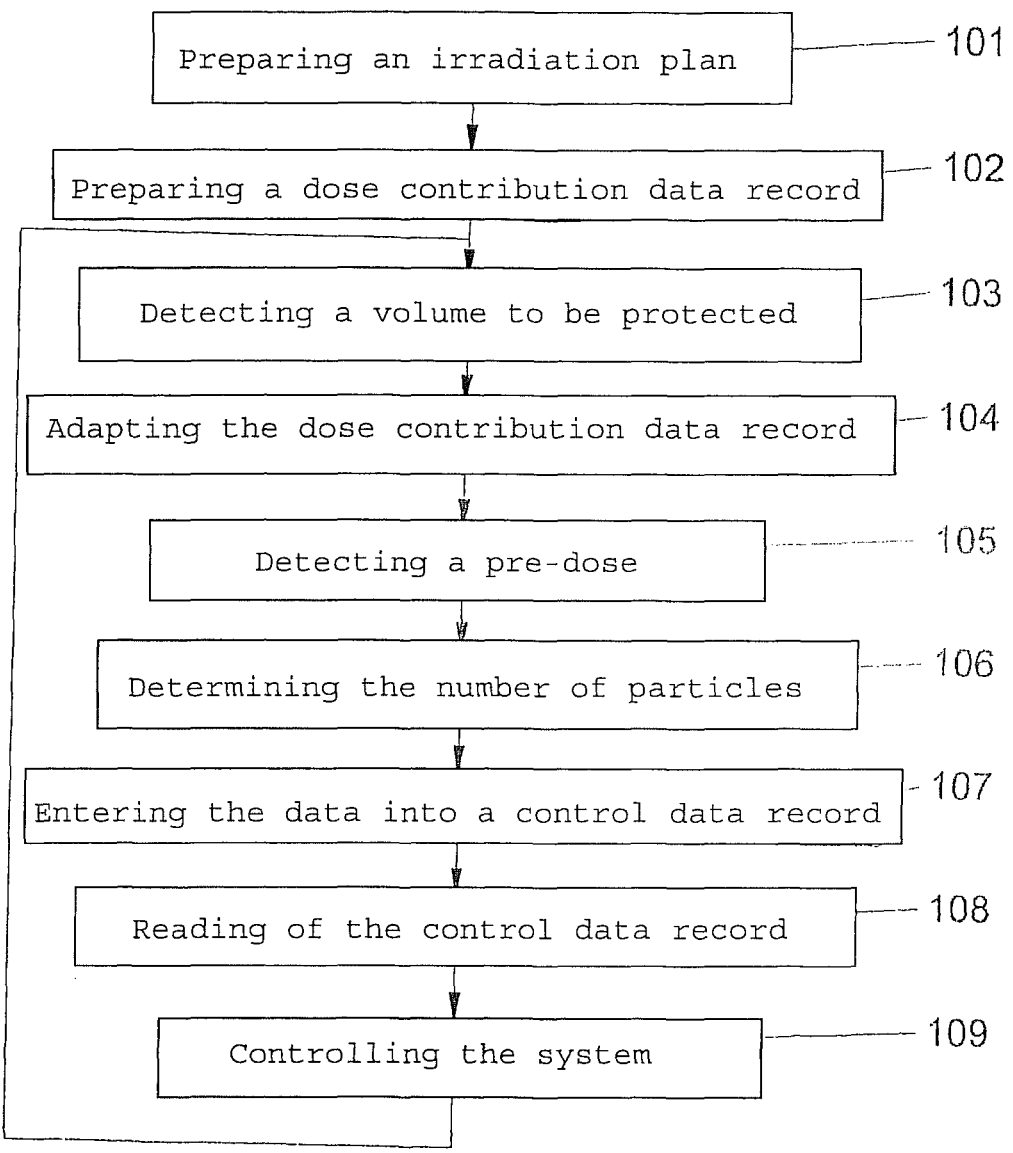

Subsequently, the invention is explained in more detail by means of embodiments and the enclosed figures. It is shown:

FIG. 1 a schematic embodiment of an irradiation system;

FIG. 2 a schematic embodiment of devices that can be used for irradiation planning, for generating a data record or for controlling an irradiation process;

FIG. 3 a schematic embodiment of target points, target volume and of a volume to be protected;

FIG. 4 a schematic embodiment of target points, target volume and of a volume to be protected;

FIG. 5 a schematic embodiment of target points, target volume and of a volume to be protected;

FIG. 6 a schematic embodiment of target points, target volume and of a volume to be protected;

FIG. 7 a schematic flow chart of a method for generating a data record and for controlling a system;

FIG. 8 a list of possible embellishing procedural steps.

FIG. 1 shows a schematic overview of the structure of an irradiation system 10 as an example for any system to be used for irradiating a body, in particular tumorous tissue in the body, with a particle beam. Particles that can be used include primarily ions, for example, protons, pions, helium ions, carbon ions, neon ions, etc.

Usually, such particles are generated in a particle source 11. If, as shown in FIG. 1, two particle sources are available, which produce two different types of ions, it is possible to switch between these two types of ions within a short interval. For this purpose, a switching magnet 12 is used which is located between the ion sources 11 and a pre-accelerator 13.

The ions generated by the one or one of the ion sources 11 and possibly selected with a switching magnet 12 are accelerated in the pre-accelerator 13 to a first energy level. For example, the pre-accelerator 13 is a linear accelerator (LINAC). Subsequently, the ions are supplied to an accelerator 15, for example, a synchrotron or cyclotron. In the accelerator 15, they are accelerated to high energies as required for irradiation. After the ions leave the accelerator 15, a high-energy beam transport system 17 guides the particle beam to one or several irradiation chambers 19. In an irradiation chamber 19, the accelerated particles are directed to a body to be irradiated. Depending on the design, this takes place from a fixed direction (in so-called fixed-beam rooms) or from different directions via a rotatable Gantry 21 that can be swiveled about an axis 22.

FIG. 2 shows a schematic embodiment of devices which can be used for irradiation planning, for generating a data record, which defines particle numbers and optionally further coordinates of target points in a target volume in a body, and for controlling an irradiation system like the one described in FIG. 1.

By means of computer tomograph or magnetic resonance tomograph 31 or by means of other diagnostic devices, it is possible to determine position and expansion of a tumor to be irradiated or any other target volume. Data from the tomograph 31 are processed immediately, or after being processed by other devices (not shown in FIG. 2), by means of a device 41 for preparing a data record. For example, the device 41 is a workplace computer, a workstation or a different computer. Furthermore, because of its user interface, software or other characteristics, the device 41 can optionally be adapted in such a way that the medical staff is able to define or view or evaluate there the target volume, the doses to be applied, the distribution of the doses to several fractions, the direction of the irradiation and other details of the particle therapy, provided the information has been predefined; if required, this information can then be adapted.

The device 10 is able to monitor a body 37 to be irradiated with differently designed control devices before, during or after the irradiation session. For example, a PET camera 32 (PET=positron emission tomography) and/or a computer tomograph (not shown in FIG. 2) are provided to detect a body 37 to be irradiated that is positioned on a hospital bed 38. The PET camera 32 and/or a distance sensor (not shown) and the hospital bed 38 can be arranged inside one of the irradiation chambers 19 described above by means of FIG. 1. In this case, it is possible to detect in the body 37 to be irradiated the dose generated by the particle beam 20, as well as position, size and shape of the target volume and a volume to be protected by means of the PET camera 32 and/or computer tomograph. Alternatively, it is possible to arrange the PET camera 32 and the hospital bed 38 outside an irradiation chamber. Alternatively or additionally, it is possible to prepare a tomography of the body 37 by means of a fluoroscopy device, an X-ray device, an ultrasound sensor and/or other devices that are able to produce three-dimensional images. The imaging method can be performed directly inside the irradiation chamber. However, it can also be performed on the outside before the patient is brought into the irradiation chamber.

The basic structure of the irradiation system 10 shown in FIG. 1 is typically for several particle therapy systems and other irradiation systems, but the irradiation system can also have a different structure. The subsequently described embodiments can be used in connection with the irradiation system described in FIG. 1 and the systems described in FIG. 2, as well as with other irradiation devices and systems.

FIG. 3 to 6 each show a diagram of a section of a cut of a body to be irradiated. Small circles of different diameters represent screen dots or target points 71 and voxels 73 which are respectively arranged in a grid. The target points 71 and the voxels 73 can each be arranged in cubical, rectangular, hexagonal or other grids. In the examples shown in FIG. 3 to 6, the grid of the target points extends only across a spatial region which comprises a region to be irradiated and does not comprise the entire body. The grid of the voxels 73 usually extends across the entire body or at least across an entire body part. However, in order to provide a clear representation and perceptibility, the grid of the voxels is only shown in FIGS. 3 and 4 and there only outside of the grid of the target points 71.

A particle beam can be directed on each of the target points 71. Based on the number of particles flowing in a particular time unit and the length of time interval wherein the particle beam is directed on the target point 71, a particle number is defined for the target point 71. Empty circles in the FIG. 3 to 6 represent target points 71 to which the particle beam is not to be directed, or to which only a small number of particles is to be applied. Filled circles represent target points 71 to which a high number of particles is to be applied.

FIG. 3 to 6 each show cut sections hatched from the top left to the bottom right through an internal region of a target volume 51. The internal regions 51 are surrounded by safety margins 52. An internal region of a target volume 51 and a safety margin 52 form together a respective target volume 53, also called a planning target volume. Organs to be protected 61 are each represented as surfaces patched from the left bottom to the right top. Each organ 61 to be protected is surrounded by a safety margin 62. An organ 61 to be protected and a safety margin 62 surrounding this organ form together a respective volume 63 to be protected. FIG. 3 to 6 show isodoses 80 which here enclose a region, wherein the dose corresponds to 95% of the maximum dose.

FIGS. 3 and 4 show respectively a cut which is oriented vertical in relation to the direction of the particle beam in two different relative spatial arrangements of the target volume 53 and the volume to be protected 63. In FIG. 3, the target volume 53 and the volume to be protected 63 are spaced apart. In FIG. 4, the distance between the internal region 51 of the planning target volume 53 and the organ 61 to be protected is reduced to the extent that the target volume 53 and the organ 63 to be protected are no longer spaced apart, but instead they are partially overlapping.

FIGS. 5 and 6 each show a cut that runs parallel to the direction of a particle beam, wherein the particle beam in the representations of FIGS. 5 and 6 incidences horizontally from the left. In both situations represented in FIGS. 5 and 6, the target volume 53 and the volume to be protected 63 are spaced apart. However, compared with the situation shown in FIG. 5, the volume to be protected 63 in the situation shown in FIG. 6 is shifted vertically upwards in relation to the target volume 63, perpendicular to the direction of the particle beam.

In the cuts shown in FIGS. 5 and 6, the density and ranges of the particle beam were inhomogeneous. In particular, the ranges were higher inside of the internal region of the planning target volume 51 than outside of the internal region of the planning target volume 51. The safety margin 52 surrounding the internal region 51 has the purpose of taking into consideration the possibility of growth or a shift of the internal region 51. Accordingly, the particle energies for all target points 71 inside the target volume 53 are determined under the assumption that the entire target volume 53 has the density of the internal region 51. When the density inside the safety margin 52 actually does not correspond to the density of the internal region 51 but corresponds to the lower density of the surrounding region, regions far behind the target volume 53 receive high doses. This can be observed at the isodose 80. In the situation shown in FIG. 6, this would result in an undesired dose in the volume 63 to be protected.

This shows that no solution, or no satisfying solution, can be obtained by merely increasing the safety margin 52, 62 to the extent that the development from the situation shown in FIG. 3 or FIG. 5 to that shown in FIG. 4 or FIG. 6 is covered from the start. However, as shown in the subsequent description with regard to FIG. 7, it is possible by specifying the numbers of particles based on an actual detection of the volume to be protected and by using a dose contribution data record to guarantee simultaneously adequate irradiation of the target volume and sufficient protection of the volume to be protected, even in the situations shown by means of FIG. 3 to 6 and in many other situations. In the situations shown in FIGS. 4 and 6, the method can result in the fact that the particle beam is no longer directed on individual target points 71, or only with a reduced number of particles.

FIG. 7 shows a schematic flow chart of a method for generating a data record and for controlling a system. Although this method can be used in other systems or with other equipment and in other situation, as those shown in FIG. 1 to 6, we will subsequently use for reasons of simplicity the reference numerals from FIG. 1 to 6.

In a first step 101, a radiation plan for irradiation in several sessions, for example, fractions, is prepared. In a second step 102, a dose contribution data record is prepared. The dose contribution data record comprises for each target point 71 and for each voxel 73 the dose contributions generated on all voxels by directing the particle beam 20 with a predetermined number of particles on the selected target point 71. For example, in the case of $n_{TP}$ target points and $n_V$ voxels, the dose contribution data record can be represented as matrix with $n_{TP}$ lines and $n_V$ columns.

In a third step 103, the volume 53 to be protected is detected, for example in tomographic manner. At the same time, it is possible to detect the target volume.

In a fourth step 104, the dose contribution data record is adapted to the actual situation detected in the third step 103. Alternatively, the dose contribution data record is newly prepared. In a simple case, especially when there are no or only minor changes, the dose contribution data record prepared in the second step 102 or any other dose contribution data record can be adopted without changes.

In an optional fifth step, a pre-dose is detected which is deposited in one or several already applied fractions. For example, this occurs by means of a numerical simulation of previous fractions, based on then existent situations and measured settings of the irradiation system. Alternatively, the dose applied in each fraction is detected already during the irradiation process, for example, by means of positron emission tomography of nuclides which emit positron and which are generated in the irradiation process.

In a sixth step 106, a number of particles is determined for each target point 71. The number of particles is determined on the basis of the current situation detected in the third step 103, in particular the position, size and shape of the volume to be protected and the target volume. Instead of the particle number, it is also possible to determine other equivalent parameters, for example, the total electrostatic charge of particles directed on the target point.

Optionally, it is also possible to consider prospective changes. Prospective changes can be estimated by an extrapolation of changes already observed. Regions of a target volume 53 which in later fractions are expected to come too close to a volume 63 to be protected, or for other reasons can no longer be irradiated without excessively exposing a volume to be protected to dose rates exceeding limit values can, for example, receive an increased or considerably increased dose already in the next fraction.

The particle numbers are determined by using the dose contribution data record prepared in the second step 102 and, optionally, by using the dose contribution data record adapted or newly prepared in the fourth step 104. For example, by using the dose contribution data record the particle numbers are iteratively optimized in such a way that to the extent possible the prescribed dose is reached within the entire target volume, and within the entire volume to be protected an upper dose limit is not exceeded. If required, the optimization can be performed in such a way that within the planning target volume, or especially within an internal region of the planning target volume, the prescribed dose is reached as fully as possible and within one or several organs at risk assigned upper dose limits are not exceeded.

Furthermore, when determining the particle numbers, it is optionally possible to consider the pre-dose detected in the fifth step 105. The dose to be applied in later fractions results from the difference of the prescribed dose, or the dose to be applied throughout all fractions, and the actual dose (calculated or measured) applied in previous fractions. In the next fraction to which the particle numbers refer, the dose to be applied in a simple case is the quotient of the dose to be applied in all prospective fractions and the number of prospective fractions. When irradiating from different directions with a respective predetermined cumulative dose, this calculation can be performed separately for each direction.

In the case shown in FIG. 4, to protect the volume to be protected, the overlapping screen dots 71 are set inactive in order to reduce the region to which high doses are applied, compare reduction of isodose. This results in the fact that the tumor volume is still covered with the dose, but the safety margin of the target volume is no longer covered.

In the case shown in FIG. 5, an inactivation of screen dots also results in a reduction of the region covered with a high dose, compare isodose. This also results in a protection of the structures at risk.

In a seventh step 107, the particle numbers determined in the sixth step 106 are entered into a data record, in particular a control data record. At the same time, it is possible to enter coordinates of the target points 71.

In an eighth step 108, the data record entered in the data record in the seventh step 107 is read. In the ninth step 109, the read data are used for controlling an irradiation system 10 by means of a control unit 46.

Preferably, the third step 103, the fourth step 104, the fifth step 105, the sixth step 106, the seventh step 107, the eighth step 108 and the ninth step 109 are repeated before or during each session, especially fraction.

FIG. 8 shows a list of developing procedural steps, which comprise:
performing irradiation in several sessions;
detecting changes of the volume to be protected and/or the target volume;
grid scanning;
tracking target points;

considering a pre-dose for determining the intensities, in particular numbers of particles;

preparing the dose contribution data record prior to the first session;

correcting the dose contribution data record after detection;

changing irradiation planning by taking into consideration a change of position and/or shape of the target volume or one of the target volumes and the volume(s) to be protected; in particular in a relative position change;

newly preparing the dose contribution data record after detection;

providing the target volume with a safety margin;

providing the volume to be protected with a safety margin;

the overlap of the safety margin of a target volume with a safety margin of a volume to be protected is not approached.

In summary, it can especially be said that the dose contributions of individual screen dots on volume elements can already be pre-calculated in irradiation planning outside of the target volume. For example, by means of the actual anatomy, it is possible to determine whether a structure at risk in comparison to irradiation planning is exposed to additional doses when the actual target volume is irradiated. In the process, a new calculation of the actual range can be made especially on a daily basis. Screen dots in which without the invention an unacceptable dose is applied to the structure at risk are for actual irradiation "post-processed," i.e., they are not irradiated or only with reduced intensity, especially a reduced number of particles.

Especially with the represented adaptive irradiation with a scanned particle beam, it is possible to perform irradiation planning in which routinely, for example, on a daily basis, the protection of a structure at risk has priority.

According to the invention, it is possible to increase the planned dose for target volumes even if a possible overdose of the structure at risk could be expected.

In order to avoid an overdose of a structure at risk without the invention, irradiation would have to be performed with a low dose or smaller safety margins.

The described embodiments are not only suitable to be used in the context of a particle therapy. In addition, they can be generally used in systems for irradiating matter, independent of whether it involves living or dead, organic or inorganic substances, a body of a patient or of an animal to be treated, a phantom, a material sample or a device.

REFERENCE LIST 10 irradiation system
11 particle source
12 switching magnet
15 pre-accelerator
17 accelerator
19 high-energy beam transport system
20 irradiation chamber
20 particle beam
21 Gantry
22 axis of the Gantry
31 tomograph
32 PET camera
37 body
38 hospital bed
41 device for preparing a data record
42 system for determining a motion parameter
46 control unit for system 10
47 control line
51 internal region
52 safety margin
53 target volume/planning target volume
61 organ to be protected/internal region
62 safety margin
63 target volume/planning target volume
71 target point
73 voxel
80 isodose
101 first step
102 second step
103 third step
104 fourth step
105 fifth step
106 sixth step
107 seventh step
108 eighth step
109 ninth step

The invention claimed is:

1. Method for planning an irradiation of a target volume in an object,
wherein individual target points are to be sequentially approached by an ion particle beam, which is pre-accelerated and then further accelerated, and
wherein irradiation intensities for each individual target point in the object are to be determined, the method comprising the following steps:
detecting a volume to be protected wherein a total dose generated by irradiating the target volume shall not exceed a predetermined maximum value,
determining the irradiation intensities for the individual target points in such a way that within the volume to be protected, the total dose does not exceed the predetermined maximum value in scheduled irradiation,
wherein a dose contribution data record is used for determining the irradiation intensities, which dose contribution data record comprises partial doses generated at other spots in the object by directing the ion particle beam in scheduled irradiation on one of the individual target points with a predetermined irradiation intensity, wherein the dose contribution data record can be used for controlling a device for irradiating the target volume using the ion particle beam,
wherein the individual target points and the other spots are arranged in a grid, and the dose contribution data record comprises for each target point and for each other spot, the dose contributions generated on the other spots by directing the ion particle beam with a predetermined number of particles on the target point,
detecting, in comparison to at least one of an original irradiation plan or a previous irradiation session, change in at least one of position, size, or shape of at least one of the volume to be protected or the target volume,
detecting an overlap of the target volume with the volume to be protected,
changing irradiation planning by taking into consideration the detected change, and
protecting the volume to be protected by setting inactive target points that overlap with the volume to be protected.

2. Method according to claim 1 wherein the irradiation is planned in several sessions.

3. Method according to claim 2, wherein the step of detecting the volume to be protected includes detecting changes in position, size and shape of at least the volume to be protected or the target volume in comparison to an original irradiation plan or in comparison to a previous session of the several sessions.

4. Method according to claim 1, wherein the planning includes grid scanning for approaching the individual target points.

5. Method according to claim 1, wherein the individual target points track structures to be irradiated.

6. Method according to claim 1, wherein the dose contribution data record is prepared prior to a first session of several sessions of irradiation.

7. Method according to claim 1, wherein the dose contribution data record is corrected on a basis of imaging methods after detecting the volume to be protected and prior to determining the intensities.

8. Method according to claim 1, wherein the dose contribution data record is newly prepared on a basis of imaging methods after detecting the volume to be protected and prior to determining the intensities.

9. Method according to claim 1, wherein a change of the target volume or the volume to be protected is taken into consideration when changing the planning of the irradiation of the target volume.

10. Method according to claim 1, wherein the target volume comprises an internal region and a safety margin surrounding the internal region, and the intensities are determined in such a way that in scheduled irradiation a dose deposited within the internal region of the target volume comprises a predetermined minimum value.

11. Method according to claim 1, wherein the volume to be protected comprises an internal region and a safety margin surrounding the internal region and furthermore the intensities are determined in such a way that in scheduled irradiation a dose deposited within the internal region of the volume to be protected does not exceed the predetermined maximum value.

12. The method set forth in claim 1, further comprising determining a number or electrostatic charge of particles for the individual target points on the basis of the detected position, size, and/or shape of the volume to be protected and/or the target volume.

13. The method set forth in claim 12, further comprising entering the determined particle number or electrostatic charge into a control data record, and using data from the control data record for controlling the device for irradiating the target volume using the ion particle beam.

14. Method according to claim 1, wherein the intensities are generated in such a way that in scheduled irradiation the beam is not directed on the individual target points within an overlap of the target volume and the volume to be protected.

15. Method for irradiating a target volume in an object, wherein irradiation intensities for individual target points in the object are determined which are sequentially approached by an ion particle beam, which is pre-accelerated and then further accelerated, the method comprising the following steps:
  detecting a volume to be protected wherein a total dose generated by irradiating the target volume should not exceed a predetermined maximum value;
  determining the irradiation intensities for the individual target points in such a way that within the volume to be protected the total dose does not exceed the predetermined maximum value,
  wherein a dose contribution data record is used for determining the irradiation intensities, which dose contribution data record comprises partial doses generated at other spots in the object by directing the ion particle beam on one of the individual target points with a predetermined irradiation intensity, wherein the dose contribution data record can be used for controlling a device for irradiating the target volume using the ion particle beam,
  wherein the individual target points and the other spots are arranged in a grid, and the dose contribution data record comprises for each target point and for each other spot, the dose contributions generated on the other spots by directing the ion particle beam with a predetermined number of particles on the target point,
  detecting, in comparison to at least one of an original irradiation plan or a previous irradiation session, change in at least one of position, size, or shape of at least one of the volume to be protected or the target volume,
  detecting an overlap of the target volume with the volume to be protected,
  changing irradiation planning by taking into consideration the detected change, and
  protecting the volume to be protected by setting inactive target points that overlap with the volume to be protected.

16. The method set forth in claim 15, further comprising determining a number or electrostatic charge of particles for the individual target points on the basis of the detected position, size, and/or shape of the volume to be protected and/or the target volume.

17. The method set forth in claim 16, further comprising entering the determined particle number or electrostatic charge into a control data record, and using data from the control data record for controlling the device for irradiating the target volume using the ion particle beam.

18. Device for irradiating a target volume in an object, comprising:
  an ion particle source and a control system for controlling the device, wherein the control system is designed to determine irradiation intensities for individual target points in the object, which are sequentially approached by an ion particle beam, which is pre-accelerated and then further accelerated, and the device is designed to detect a volume to be protected, wherein a total dose generated by irradiating the target volume should not exceed a predetermined maximum value;
  to determine the irradiation intensities for the individual target points in such a way that within the volume to be protected the generated total dose does not exceed the predetermined maximum value, wherein a dose contribution data record is used for determining the irradiation intensities, which dose contribution data record comprises partial doses generated at other spots in the object by directing the ion particle beam on one of the individual target points with a predetermined intensity, wherein the dose contribution data record can be used for controlling the device for irradiating the target volume using the ion particle beam,
  wherein the individual target points and the other spots are arranged in a grid, and the dose contribution data record comprises for each target point and for each other spot, the dose contributions generated on the other spots by directing the ion particle beam with a predetermined number of particles on the target point,
  a detection system for detecting, in comparison to at least one of an original irradiation plan or a previous irradiation session, change in at least one of position, size, or shape of at least one of the volume to be protected or the target volume, and for detecting an overlap of the target volume with the volume to be protected, changing irradiation planning by taking into consideration the detected change, and protecting the volume to be protected by setting inactive target points that overlap with the volume to be protected.

19. Device according to claim 18, designed for performing a method for planning an irradiation or a method for irradiation of a target volume in an object, wherein individual target points are to be sequentially approached by an ion particle beam, which is pre-accelerated and then further accelerated, and wherein irradiation intensities for each individual target point in the object are to be determined, the method comprising the following steps, detecting a volume to be protected wherein a total dose generated by irradiating the target volume shall not exceed a predetermined maximum value, determining the irradiation intensities for the individual target points in such a way that within the volume to be protected, the total dose does not exceed the predetermined maximum value in scheduled irradiation, wherein a dose contribution data record is used for determining the irradiation intensities, which dose contribution data record comprises partial doses generated at other spots in the object by directing the ion particle beam in scheduled irradiation on one of the individual target points with a predetermined irradiation intensity, wherein the dose contribution data record can be used for controlling a device for irradiating the target volume using the ion particle beam, wherein the individual target points and the other spots are arranged in a grid, and the dose contribution data record comprises for each target point and for each other spot, the dose contributions generated on the other spots by directing the ion particle beam with a predetermined number of particles on the target point, detecting, in comparison to at least one of an original irradiation plan or a previous irradiation session, change in at least one of position, size, or shape of at least one of the volume to be protected or the target volume, detecting an overlap of the target volume with the volume to be protected, changing irradiation planning by taking into consideration the detected change, and protecting the volume to be protected by setting inactive target points that overlap with the volume to be protected.

20. Control system for controlling a device for irradiating a target volume in an object, wherein the device is designed by means of the control system to determine irradiation intensities for individual target points in the object which are sequentially approached by an ion particle beam, which is pre-accelerated and then further accelerated, to detect a volume to be protected, wherein a total dose generated by irradiating the target volume should not exceed a predetermined maximum value; to determine the irradiation intensities for the individual target points in such a way that within the volume to be protected the generated total dose does not exceed the predetermined maximum value, wherein a dose contribution data record is used for determining the irradiation intensities, which dose contribution data record comprises partial doses generated at other spots in the object by directing the ion particle beam on one of the individual target points with a predetermined intensity, wherein the dose contribution data record can be used for controlling the device for irradiating the target volume using the ion particle beam, wherein the individual target points and the other spots are arranged in a grid, and the dose contribution data record comprises for each target point and for each other spot, the dose contributions generated on the other spots by directing the ion particle beam with a predetermined number of particles on the target point, detecting, in comparison to at least one of an original irradiation plan or a previous irradiation session, change in at least one of position, size, or shape of at least one of the volume to be protected or the target volume, detecting an overlap of the target volume with the volume to be protected, changing irradiation planning by taking into consideration the detected change, and protecting the volume to be protected by setting inactive target points that overlap with the volume to be protected.

* * * * *